US007285292B2

(12) United States Patent
Laurie et al.

(10) Patent No.: US 7,285,292 B2
(45) Date of Patent: Oct. 23, 2007

(54) TRACE ELEMENTS

(75) Inventors: Robert Naylor Laurie, Somerset West (ZA); William Alfred Smith, Porterville, CA (US)

(73) Assignee: Warburton Technology Limited, Dublin (IE)

( * ) Notice: Subject to any disclaimer, the term of this patent is extended or adjusted under 35 U.S.C. 154(b) by 403 days.

(21) Appl. No.: 10/834,094

(22) Filed: Apr. 29, 2004

(65) Prior Publication Data

US 2005/0244511 A1 Nov. 3, 2005

(51) Int. Cl.
| | |
|---|---|
| A61K 33/00 | (2006.01) |
| A61K 33/04 | (2006.01) |
| A61K 33/18 | (2006.01) |
| A61K 33/24 | (2006.01) |
| A61K 33/26 | (2006.01) |
| A61K 33/30 | (2006.01) |
| A61K 33/32 | (2006.01) |
| A61K 33/34 | (2006.01) |
| A61K 31/194 | (2006.01) |
| A61K 31/28 | (2006.01) |
| A61K 31/295 | (2006.01) |
| A61K 31/30 | (2006.01) |
| A61P 7/08 | (2006.01) |

(52) U.S. Cl. .................. 424/634; 424/630; 424/632; 424/633; 424/635; 424/637; 424/638; 424/639; 424/640; 424/641; 424/643; 424/646; 424/647; 424/648; 424/655; 424/656; 424/667; 424/669; 424/670; 424/671; 424/702; 424/DIG. 6; 514/492; 514/494; 514/499; 514/500; 514/706; 514/836

(58) Field of Classification Search ............... 424/630, 424/634, 639, 641, 643, 655, 702
See application file for complete search history.

(56) References Cited

U.S. PATENT DOCUMENTS

| 4,335,116 | A | | 6/1982 | Howard | |
|---|---|---|---|---|---|
| 5,443,847 | A | * | 8/1995 | West | 424/639 |
| 5,543,432 | A | * | 8/1996 | Harvey | 514/630 |
| 6,416,782 | B1 | * | 7/2002 | Maas | 424/438 |
| 6,638,539 | B2 | | 10/2003 | Laurie et al. | |

| 2002/0068079 | A1 | * | 6/2002 | Laurie et al. | 424/422 |

FOREIGN PATENT DOCUMENTS

| DE | 41 28 760 | | 3/1992 |
|---|---|---|---|
| DE | 196 17 185 | | 10/1997 |
| JP | 2000-178181 | * | 6/2000 |
| WO | WO 83/01559 | | 5/1983 |
| ZA | 1982/6778 | | 9/1982 |

OTHER PUBLICATIONS

The European Agency for the Evaluation of Medicinal Products, Committee For Veterinary Medicinal Products, Summary Report. Chlorocresol [online], pp. 1-3, Mar. 1996 [retrieved on Jan. 18, 2007]. Retrieved from the Internet: <URL: http://www.emea.eu.int/pdfs/vet/mrls/007496en.pdf>.*
Derwent Abstract 2000-527656; abstracting JP 2000178181 (2000).*
Trengove et al., "Trace element supplementation of sheep: evaluation of various copper supplements . . . ", Australian Veterinary Journal, vol. 62, No. 10, Oct. 1985.
Koenig et al., "Effects of Diet and Chemical Form of Selenium on Selenium Metabolism in Sheep", J. Anim. Sci. 1997, 75:817-827.
Allen et al., "Parenteral methods of supplementation with copper and selenium", The Veterinary Record, May 6, 1984, pp. 451-454.
Edmiston et al., "Evaluation of Selenium Reticular Pellets and Injectable Copper Edetate for Yearling Replacement Heifers", American Society of Animal Science, 1988, vol. 39, pp. 111-114.

* cited by examiner

*Primary Examiner*—John Pak
(74) *Attorney, Agent, or Firm*—B. Aaron Schulman; Stites & Harbison PLLC

(57) ABSTRACT

The invention discloses a trace element solution, which comprises at least one metal selected from the group comprising selenium, copper, zinc, manganese and chromium and which comprises a concentration of the metal(s) of at least 60 mg/ml. The solution further comprises at least one compound selected from the group comprising iodine, potassium iodide, sodium iodide, iron, iron chloride, zinc oxide, manganese sulphate, sodium selenite, copper carbonate, sodium carbonate, anhydrous disodium EDTA and sodium hydroxide. The trace element solution is prepared by a method consisting essentially of the steps of preparing a $MnCO_3$ mixture in a container; adding an EDTA/NaOH mixture to the container and subsequently adding at least one metal compound; and adding $Na_2SeO_3$ to the container to obtain the trace element solution. The method also comprises the step of adding $CrCl_3.6H_2O$ to the trace element solution.

23 Claims, No Drawings

TRACE ELEMENTS

FIELD OF INVENTION

The present invention relates to trace elements.

BACKGROUND TO INVENTION

It has been found that there is a deficiency of certain trace elements in pastures for livestock in particular areas around the world. Various suggestions have been made to provide the required trace elements to such animals. Different chemical compounds and complexes have been investigated for applying the trace elements by way of licks, drenches or injections.

In general the problem with injectable solutions is that there are too low concentrations of the minerals in the solutions. This means that relatively large quantities have to be injected, which in turn causes tissue damage and also abscesses at the site of injection. Furthermore, it is generally the case that different trace elements seldomly are individually sufficient. This means that two or more trace element solutions have to be provided by way of separate injections.

ZA 1982/6778 (Laurie) discloses a trace element solution and a method of providing the trace elements to livestock. These trace element solution include ethylene diamino tetra acetic acid complex of the required mineral in suitable quantities. However, the trace element solution includes no selenium or selenite compound.

In the specification and claims the expression EDTA refers to ethylene diaminotetraacetic acid ($C_{10}H_{16}O_8N_2$ or $(HO_2CH_2C)_2NCH_2CH_2N—(CH_2CO_2H)_2$).

U.S. Pat. No. 4,335,116 (Howard) discloses mineral-containing therapeutic compositions containing EDTA complexes of trace elements. Notably, U.S. Pat. No. 4,335,116 utilises tetra-sodium EDTA, a selenium glycine complex, and metal chlorides for the preparation of the EDTA complexes. Unfortunately, the chloride ions cause contamination and each complex solution is to be made individually. Furthermore, overnight time is required for complexing and heating up afterward to speed up the process, requires extra apparatus. If mixtures are required, the individual solutions are to be blended. If various concentrations as well as compositions are to be made, it can only be done in a cumbersome way, requiring extra apparatus. A further problem may arise when mixtures of high concentration are needed. In certain cases it would be impossible to deliver them, because mixing is always accompanied by dilution.

U.S. Pat. No. 6,638,539 (Laurie et al) discloses a method of preparing a trace element solution, which includes the steps of providing at least one EDTA-complex, of providing a sodium selenite solution, and of combining the EDTA-complexes and the sodium selenite solution. However, the method enables production of a trace element solution of only about 55 mg/ml.

It is an object of the invention to suggest methods and means for overcoming these problems.

SUMMARY OF INVENTION

According to the invention, a trace element solution, which comprises at least one metal selected from the group comprising selenium, copper, zinc, manganese and chromium and which comprises a concentration of the metal(s) of at least 60 mg/ml.

The solution may comprise at least one compound selected from the group comprising iodine, potassium iodide, sodium iodide, iron, iron chloride, zinc oxide, manganese sulphate, sodium selenite, copper carbonate, sodium carbonate, anhydrous disodium EDTA and sodium hydroxide.

At least one of the metal(s) may be provided in the form of an EDTA complex.

The EDTA complex may be obtained by means of at least one compound selected from the group comprising sodium EDTA and potassium EDTA.

The solution may comprise chloro-cresol as preservative.

The solution may be prepared in a continuous batch process.

The solution may be an injectable solution.

The solution may be a drenchable solution.

Also according to the invention, a method of preparing a trace element solution comprising at least one metal selected from the group comprising selenium, copper, zinc, manganese and chromium and comprising a concentration of the metal(s) of at least 60 mg/ml, said method consisting essentially of the steps of:

(a) preparing a $MnCO_3$ mixture in a container;
(b) adding an EDTA solution to the container and subsequently adding at least one metal compound; and
(c) adding $Na_2SeO_3$ to the container to obtain the trace element solution.

The EDTA solution may be selected from the group comprising a potassium EDTA solution and a sodium EDTA solution.

The method may comprise the step of adding $CrCl_3.6H_2O$ to the trace element solution.

The method may comprise the step of adding a EDTA/NaOH mixture prior to addition of the $CrCl_3.6H_2O$ to the trace element solution.

The method may comprise the step of adjusting the pH of the trace element solution to 6,7 to 7,0.

The method may comprise the step of adjusting the pH of the trace element solution by adding at least one compound selected from the group comprising NaOH and EDTA.

The trace element solution may be diluted.

The temperature of the $MnCO_3$ mixture may be at least 60 degrees Celsius.

Water having a temperature of at least 70 degrees Celsius may be added to the $MnCO_3$ mixture.

The addition of the EDTA/NaOH mixture may occur gradually with small quantities.

The method may comprise the step of cooling the trace element solution prior to addition of the $Na_2SeO_3$.

The $MnCO_3$ mixture may be prepared by mixing $MnSO_4$ and $Na_2CO_3$.

The metal compound may be selected from the group comprising ZnO, $CuCO_3$, $Na_2CO3$, $MnSO_4$ and $FeCl_3$.

The metal compound may be selected from the group comprising metal oxides, metal hydroxides and metal carbonates.

Yet further according to the invention, a trace element solution as prepared by the above method.

Yet further according to the invention, a stock lick, which comprises a trace element solution as prepared by the method above.

Yet further according to the invention, a method of providing trace elements to animals, such as livestock, which comprises the steps of preparing a trace element solution as described above and of providing the solution in a suitable quantity to an animal.

Yet further according to the invention, an injectable trace element solution, which comprises at least one compound selected from the group comprising iodine, potassium iodide and sodium iodine and which comprises a concentration of the compound(s) of at least 20 mg/ml.

Yet further according to the invention, a trace element solution, which comprises at least one compound selected from the group comprising chromium and $CrCl_3.6H_2O$.

Yet further according to the invention, a trace element solution, which
(a) comprises at least one metal selected from the group comprising selenium, copper, zinc, manganese and chromium;
(b) comprises a concentration of the metal(s) of at least 60 mg/ml;
(c) comprises at least one of the metal(s) provided in the form of an EDTA complex; and
(d) which is obtained by at least one compound selected from the group comprising iodine, potassium iodide, sodium iodide, iron, iron chloride, zinc oxide, manganese sulphate, sodium selenite, copper carbonate, sodium carbonate, anhydrous disodium EDTA and sodium hydroxide.

Yet further according to the invention, a method of preparing a trace element solution comprising at least one metal selected from the group comprising selenium, copper, zinc, manganese and chromium and comprising a concentration of the metal(s) of at least 60 mg/ml, said method consisting essentially of the steps of:
(a) preparing a $MnCO_3$ mixture in a container at a temperature of at least 60 degrees Celsius;
(b) adding an EDTA solution to the container and subsequently adding at least one metal compound selected from the group comprising ZnO, $CuCO_3$, $Na_2CO_3$, $MnSO_4$ and $FeCl_3$;
(c) adding at least compound selected from the group comprising $Na_2SeO_3$ and $CrCl_3.6H_2O$ to the container to obtain the trace element solution; and
(d) adjusting the pH of the trace element solution.

Yet further according to the invention, a trace element solution, which comprises
(a) 35-50 mg/ml of zinc;
(b) 10-15 mg/ml manganese;
(c) 5-10 mg/ml selenium; and
(d) 10-20 mg/ml copper.

The solution may comprise 5-10 mg/ml chromium.
The solution may comprise 5-50 mg/ml iron.
The solution may comprise 20-400 mg/ml iodine.

DESCRIPTION OF EXAMPLES

The invention will now be described by way of example of injectable solutions in accordance with the invention.

Example 1

Example 1 relates to a method to prepare a trace element solution predominantly to be used for cattle and includes the mineral elements Selenium, Copper and Chromium.

The method enables preparation of 25 litres of the solution containing 40 mg Zn, 10 mg Mn, 5 mg Se, 15 mg Cu and 5 mg Cr per ml.

A. Preparing $MnCO_3$

In a suitable container/drum, the $MnCO_3$ mud is prepared by adding solutions of 900 g $MnSO_4$ and 1150 g $Na_2CO_3$ together. The resultant mixture is decanted and washed three times.

B. Continuous Batch Process

To the $MnCO_3$ mud, hot water (70° C.) is added to a volume of at least 15 litres. Critical is the temperature at the start of the batch process which should be at least 60° C.

B.1 Preparing MnEDTA 2000 g EDTA and 500 g NaOH are weighed; the EDTA and NaOH are mixed; the EDTA/NaOH mixture is added to the drum, in small quantities to prevent excessive frothing, until the reaction is complete (leaving a clear pinkish solution).

B.2 Preparing ZnEDTA (2 Steps)

Step 1:

2600 g EDTA, 690 g NaOH and 700 g ZnO are weighed, the EDTA and NaOH are mixed and ZnO is kept separate. The EDTA/NaOH mixture is added to the drum in small quantities to prevent boiling over, followed by addition of the ZnO. The reaction is allowed to complete (again leaving a clear pink solution). The temperature at this stage could reach 103° C.

Step 2:

2600 g EDTA, 690 g NaOH and 700 g ZnO are weighed. The EDTA and NaOH are mixed and the ZnO kept separate. The EDTA/NaOH mixture is added to the drum in small quantities to prevent boiling over, where after the ZnO is added. The reaction is allowed to complete (again leaving a clear pink solution). The temperature at this stage could reach 103° C.

B.3 Preparing CuEDTA 1760 g EDTA, 462 g NaOH and 693 g basic $CuCO_3$ are weighed. The EDTA and NaOH are mixed and the $CuCO_3$ kept separate. The EDTA/NaOH mixture is added to the drum, followed by careful addition of the $CuCO_3$, to prevent excessive frothing, and the reaction is allowed to complete (leaving a clear blue solution).

B.4 25 g chlorocresol is added and stirred till dissolved.

B.5 23 litres is made up

B.6 The mixture is allowed to cool to room temperature.

C. Final Phase

C.1 303 g $Na_2SeO_3$ is added.

C.2 The pH is adjusted to 6,7 by adding NaOH (40% solution) or EDTA.

C.3 738 g EDTA, 192 g NaOH and 641 g $CrCl_3.6H_2O$ are weighed. The EDTA and NaOH are mixed and added to the drum. The $CrCl_3.6H_2O$ is added, whereby the reaction is slow.

C.4 The volume is made up to 25 litres.

Example 2

Example 2 relates to a method to prepare a trace element solution predominantly to be used for sheep and includes the mineral elements Selenium and Copper.

The method enables preparation of 100 litres of the solution containing 40 mg Zn, 10 mg Mn, 3 mg Se and 10 mg Cu per ml.

A. Preparing $MnCO_3$

In a suitable container/drum, the $MnCO_3$ mud is prepared by adding solutions of 3600 g $MnSO_4$ and 4600 g $Na_2CO_3$ together. The mixture is decanted and wash three times.

B. Continuous Batch Process

To the $MnCO_3$ mud, is added hot water (70° C.) to a volume of at least 60 litres. The temperature at the start of the batch process is critical and should be at least 60° C.

B.1 Preparing MnEDTA 8000 g EDTA and 2000 g NaOH are weighed. The EDTA and NaOH are mixed. The EDTA/NaOH mixture is added to the drum, in small quantities to prevent excessive frothing, until the reaction is complete (leaving a clear pinkish solution).

B.2 Preparing ZnEDTA (2 Steps)

Step 1:

10400 g EDTA, 2760 g NaOH and 2800 g ZnO are weighed. The EDTA and NaOH are mixed and the ZnO kept separate. The EDTA/NaOH mixture is added to the drum in small quantities to prevent boiling over, followed by addition of the ZnO. The reaction is allowed to complete (again leaving a clear pink solution). The temperature at this stage could reach 103° C.

Step 2:

10400 g EDTA, 2760 g NaOH and 2800 g ZnO are weighed. The EDTA and NaOH are mixed and the ZnO kept separate. The EDTA/NaOH mixture is added to the drum in small quantities to prevent boiling over, followed by addition of the ZnO.

The reaction is allowed to complete (again leaving a clear pink solution). The temperature at this stage could reach 103° C.

B.3 Preparing CuEDTA 4646 g EDTA, 1220 g NaOH and 1835 g basic $CuCO_3$ are weighed. The EDTA and NaOH are mixed and the $CuCO_3$ kept separate. The EDTA/NaOH mixture is added to the drum, followed by careful addition of the $CuCO_3$, to prevent excessive frothing, and the reaction is allowed to complete (leaving a clear blue solution).

B.4 100 g chlorocresol is added and the mixture stirred until dissolved.

B.5 The volume is made up to 96 litres

B.6 The mixture is cooled to room temperature.

C. Final Phase

C.1 728 g $Na_2SeO_3$ is added.

C.2 The pH is adjusted to 6,7 by adding NaOH (40% solution) or EDTA.

C.3 The volume is made up to 100 litres.

Example 3

Example 3 relates to a method to prepare a trace element solution predominantly to be used for cattle and includes the mineral elements Selenium and Copper.

The method enables preparation of 100 litres of the solution containing 40 mg Zn, 10 mg Mn, 5 mg Se and 15 mg Cu per ml.

A. Preparing $MnCO_3$

In a suitable container/drum, the $MnCO_3$ mud is prepared by adding solutions of 3600 g $MnSO_4$ and 4600 g $Na_2CO_3$ together. The mixture is decanted and wash three times.

B. Continuous Batch Process

To the $MnCO_3$ mud, hot water (70° C.) is added to a volume of at least 60 litres. The temperature at the start of the batch process is critical and should be at least 60° C.

B.1 Preparing MnEDTA 7840 g EDTA and 1960 g NaOH are weighed. The EDTA and NaOH are weighed. The EDTA/NaOH mixture is added to the drum, in small quantities to prevent excessive frothing, until the reaction is complete (leaving a clear pinkish solution).

B.2 Preparing ZnEDTA (2 Steps)

Step 1:

10400 g EDTA, 2760 g NaOH and 2800 g ZnO are weighed. The EDTA and NaOH are mixed and the ZnO kept separate. The EDTA/NaOH mixture is added to the drum, in small quantities to prevent boiling over, followed by addition of the ZnO. The reaction is allowed to complete (again leaving a clear pink solution). The temperature at this stage could reach 103° C.

Step 2:

10400 g EDTA, 2760 g NaOH and 2800 g ZnO are weighed. The EDTA and NaOH are mixed and the ZnO kept separate. The EDTA/NaOH mixture is added to the drum, in small quantities to prevent boiling over, followed by addition of the ZnO.

The reaction is allowed to complete (again leaving a clear pink solution). The temperature at this stage could reach 103° C.

B.3 Preparing CuEDTA 7040 g EDTA, 1848 g NaOH and 2780 g basic $CuCO_3$ are weighed. The EDTA and NaOH are mixed and the $CuCO_3$ kept separate. The EDTA/NaOH mixture is added to the drum, followed by careful addition of the $CuCO_3$, to prevent excessive frothing, and the reaction is allowed to complete (leaving a clear blue solution).

B.4 100 g chlorocresol is added and the mixture stirred till dissolved.

B.5 The mixture is made up to 96 litres

B.6 The mixture is allowed to cool to room temperature.

C. Final Phase

C.1 1212 g $Na_2SeO_3$ is added.

C.2 The pH is adjusted to 7,0 by adding NaOH (40% solution) or EDTA.

C.3 The volume is made up to 100 litres.

General

The invention therefore provides a trace element solution which is tissue friendly, i.e. is not damaging or irritant to the tissue of animals and which comprises selenium, copper, zinc, manganese, iron and chromium and at a concentration of the metals of at least 60 mg/ml. The trace elements in solution are in a scientifically formulated ratio according to the post-absorption requirements of the animals calculated according to provided As an example the trace element solution comprises (a) 35-50 mg/ml of zinc;
(b) 10-15 mg/ml manganese;
(c) 5-10 mg/ml selenium;
(d) 10-20 mg/ml copper;
(e) 5-10 mg/ml chromium;
(f) 5-50 mg/ml iron; and
(g) comprises 20-400 mg/ml iodine.

The iodine is provided in the form of potassium iodide or sodium iodide and the iron is provided in the form of iron chloride.

The method of preparing a trace element solution in accordance with the invention thus enables the production of a solution comprising an adequate trace mineral concentration so that a 5 to 10 milliliter injection can make a significant impact on the trace mineral status of the animal, i.e. a practically applicable injectable supplement and a product that can improve the trace mineral status of an animal is provided. This is important as livestock producers will only inject livestock if a real benefit can be demonstrated. Furthermore, the subcutaneous injection is the preferred route to minimize tissue damage

The invention claimed is:

1. An injectable trace element solution for livestock, said solution comprising:
   (a) 3-10 mg/ml selenium provided in at least one of the forms selected from the group consisting of selenite and selenate
   (b) 35-50 mg/ml zinc;
   (c) manganese; and
   (d) at least one metal selected from the group consisting of copper, iron and chromium;
   the solution having a total concentration of selenium, zinc, manganese and at least one of copper, iron and chromium of at least 60 mg/ml.

2. The solution of claim 1, further comprising iodine.

3. The solution of claim 2, wherein iodine is provided in at least one of the forms selected from the group consisting of potassium iodide and sodium iodide.

4. The solution of claim 2, wherein the iodine is present at a concentration of between 20 to 400 mg/ml.

5. The solution of claim 1, wherein at least one of selenium, zinc, manganese, copper, iron or chromium is provided in the form of an EDTA complex, with the EDTA complex obtained by means of at least one compound selected from the group consisting of sodium EDTA, potassium EDTA, and a combination of sodium hydroxide and EDTA acid.

6. The solution of claim 1, wherein the solution contains chromium.

7. The solution of claim 1, wherein copper is present at a concentration of 10-20 mg/ml.

8. The solution of claim 6, wherein the chromium is provided in the form of $CrCl_3 \cdot 6H_2O$.

9. The solution of claim 1, wherein iron is present at a concentration of 5-50 mg/ml.

10. The solution of claim 1, wherein the manganese is present at a concentration of 10-15 mg/ml.

11. A method of preparing an injectable trace element solution for livestock, which is prepared in a continuous batch process, the method comprising:
    (a) providing selenium in at least one of the forms selected from the group consisting of selenite and selenate;
    (b) providing zinc in the container;
    (c) providing manganese in the container;
    (d) providing at least one of the metals selected from the group consisting of copper, iron and chromium in the container;
    wherein the provided ingredients in (a), (b), (c) and (d) are in sufficient amount in solution to provide an injectable trace element solution having 3-10 mg/ml selenium, 35-50 mg/ml zinc, manganese and at least one metal selected from the group consisting of copper, iron and chromium, the injectable trace element solution having a total concentration of selenium, zinc, manganese and at least one of copper, iron and chromium of at least 60 mg/ml.

12. The method of claim 11, further comprising adding $CrCl_3 \cdot 6H_2O$ to the injectable trace element solution.

13. The method of claim 11, further comprising adjusting the pH of the injectable trace element solution to 6.7 to 7.0.

14. The method of claim 11, further comprising adjusting the pH of the injectable trace element solution by adding at least one compound selected from the group consisting of NaOH and EDTA.

15. The method of claim 11, further comprising adding water to the container.

16. The method of claim 11, further comprising adding water having a temperature of at least 70° C. to the container.

17. The method of claim 11, wherein at least one of metals in (b), (c) or (d) is provided in the form of ZnO, $CuCO_3$, $CuSO_4$, $MnSO_4$, $FeCl_3$ and $MnCO_3$.

18. The method of claim 11, further comprising providing manganese in the form of $MnCO_3$, which is prepared by mixing $MnSO_4$ and $Na_2CO_3$.

19. A method of providing trace elements to animals, said method comprising preparing an injectable trace element solution by the method as claimed in claim 11, and providing the solution in a suitable quantity to an animal.

20. The method of claim 19, wherein said animal to which the solution is provided is a livestock animal.

21. The method of claim 11, wherein the injectable trace element solution contains manganese at a concentration of 10-15 mg/ml.

22. The method of claim 11, wherein at least one of ingredients (a), (b), (c) and (d) is provided in the form of an EDTA complex, with the EDTA complex obtained by means of at least one compound selected from the group consisting of sodium EDTA, potassium EDTA, and a combination of sodium hydroxide and EDTA acid.

23. The method of claim 22, wherein EDTA acid/NaOH mixture is added gradually in small quantities.

* * * * *